United States Patent [19]

Trautman et al.

[11] Patent Number: 4,676,252

[45] Date of Patent: Jun. 30, 1987

[54] DOUBLE INDICATOR PULMONARY EDEMA MEASUREMENT

[75] Inventors: Edwin D. Trautman, Newton; Ronald S. Newbower, Acton, both of Mass.

[73] Assignee: Massachusetts General Hospital, Boston, Mass.

[21] Appl. No.: 786,341

[22] Filed: Oct. 9, 1985

Related U.S. Application Data

[63] Continuation of Ser. No. 270,788, Jun. 5, 1981, abandoned.

[51] Int. Cl.$^4$ ............................................. A61B 5/08
[52] U.S. Cl. ................................... 128/671; 128/716; 128/692
[58] Field of Search ............................... 128/671, 716

[56] References Cited

U.S. PATENT DOCUMENTS 4,230,126  10/1980  Elings ............................. 128/692 X

FOREIGN PATENT DOCUMENTS 621344  8/1978  U.S.S.R. ............................. 128/692

OTHER PUBLICATIONS

Trautman, E. D., "Multiple Indicator Dilution Measurements of Pulmonary Edema Using Simultaneous Electrical Conductivity and Thermal Sensing In Blood", Doctoral Thesis, Mass. Inst. of Technology, Feb. 1980.

Bourdillon, P. J. et al. "Saline Conductivity Method for Measuring Cardiac Output Simplified", MBE, vol. 17, No. 3, May 1979, pp. 323-330.

Noble, W. H. et al., "Thermal and Conductivity Dilution Curves for Rapid Quantitation of Pulmonary Edema", Journal of Applied Physiology, vol. 32, No. 6, Jun. 1972.

*Primary Examiner*—Kyle L. Howell
*Assistant Examiner*—Francis J. Jawarski
*Attorney, Agent, or Firm*—Weingarten, Schurgin, Gagnebin & Hayes

[57] ABSTRACT

Patient monitoring method and apparatus for measurement of in vivo extra vascular lung water (pulmonary edema) and pulmonary circulatory system thermal bypass utilizing double indicator dilution with temperature and electrical conductivity modifiers. A thermal modifier is utilized for a primary indicator dilution measurement with electrical conductivity provided as a reference indicator which in turn is corrected for temperature effects produced by the thermal moderator as well as effects of plasma characteristics. Thermal and conductivity sensors are both placed upstream and downstream of the lungs in the pulmonary artery and thesystemic arterial system, and a thermal and conductivity moderator is injected at a site upstream from both. Temperature and conductivity are detected at both sites and the conductivity signal is converted to a volume dilution valve. Lung water is then determined as a function of the mean transit time difference of the two sensed temperatures less the mean transit time difference for the two conductivity based volume dilutions. Because the measurement is based on four sensors and mean transit time differences are used, in vivo error sources merely act as more signal and do not affect the final values. The detected signals are also analyzed in a manner to yield information on thermal bypass. The measurement technique disclosed is useful in correcting the effects of a conductivity indicator for thermal and blood effects however employed.

20 Claims, 4 Drawing Figures

DOUBLE INDICATOR PULMONARY EDEMA MEASUREMENT

The invention described herein was made in the course of work under a grant or award from the Department of Health and Human Services.

This application is a continuation of application Ser. No. 270,788, filed June 5, 1981 now abandoned.

FIELD OF THE INVENTION

The present invention relates to indicator dilution measurments in vivo and in particular to thermal and electrical conductivity double indicator dilution measurements useful in quantifying pulmonary edema and indicating thermal bypass.

BACKGROUND OF THE INVENTION

The characteristics of a generally inaccessible body through which a fluid flows can in many cases be determined by adding to the fluid flow upstream of the body an injectant which modifies a property of the fluid and detecting, over time, the modified property downstream of the body. One particular example of this is in the field of medicine in which the onset of pulmonary edema or lung water is to be detected in vivo in advance of the lung water accumulation reaching the point where it severely affects the patient and is thus detectable through other less sensitive means.

Techniques of indicator dilution have been utilized for several decades in clinical research in an effort to detect the onset of pulmonary edema which may typically occur at times following serious surgery. Indicator dilution measurements have typically involved injecting into the blood a modifier of thermal, conductivity, radioactive or dye properties of the blood in the pulmonary artery with the indicator passing through the pulmonary vascular network where it may be detected downstream of the pulmonary vein, typically after passage through the left heart, where catheter mounted detection sensors may be readily placed or blood samples withdrawn for dye marker or radioisotope detection. This technique operates on the relative tendencies of the lung water mass to reversibly absorb or not absorb indicator as it flows through the pulmonary vascular network. In particular, the use of an indicator such as heat which is readily diffusable into the high specific mass of lung water is advantageously combined with a less diffusable indicator such as an appropriate conductivity modifier or dye marker.

The success of such techniques has been substantially limited by the complexity of the response of the pulmonary and cardiovascular system to different types of indicators as well as the difficulty of accessing living patient's organs in vivo for empirical analyses. Blood temperature, plasma solute ions and proteins, hematocrit and osmolality properties as well as heat diffusion paths other than through lung water of the full pulmonary circulatory system are felt to affect the sensed indicator magnitudes in ways which are not thoroughly understood or predictable. In addition, noise errors may appear in the detected signals such as from indicator recirculation. These tend to seriously affect the value of early lung water detection by indicator dilution and preclude the detection of lung water in absolute terms as opposed to relative values.

BRIEF SUMMARY OF THE INVENTION

Careful modeling of the pulmonary circulatory system and of the response of blood and surrounding tissue to various indicators has lead to a method for processing thermal and conductivity double indicator dilution signals to provide a more accurate quantification of extra vascular lung water as an indication of pulmonary edema. In addition, a monitoring technique based on double indicator mean transit time differences provides a noise immune technique for lung water monitoring.

Thermal and conductivity sensors are, according to the teaching of the present invention, each placed within the pulmonary artery and the systemic arterial system by standard catheter placement techniques. A double indicator such as a cold saline, providing both a thermal and conductivity modification to blood, is applied typically in one vena cava from which it is pumped by the right heart into the pulmonary vascular system and returned through the left heart to the aorta and the systemic arterial system. After injection of the thermal and conductivity modifier, two thermal signals and two conductivity signals, one each from the pulmonary artery and the systemic arterial system, are detected over a time span of approximately half a minute. The conductivity signals are converted to volume dilution values, a measure of indicator concentration as a volume fraction of the total volume of indicator and blood. The conversion includes providing the volume dilution value as a function not only of sensed conductivity but also as function of blood properties and of temperature itself. The blood properties may either be determined by prior blood sampling techniques or by a sample taken through the injection catheter by a withdrawal mechanism. Mean transit times for the temperature values and conductivity volume dilution values are then determined as the ratios of time to area integrals. The product of the difference in mean transit times with the flow of heat capacity yields a measure of extravascular heat capacity. This is converted to extravascular lung water by a function of body weight. The resulting lung water value provides an accurate assessment of the degree of pulmonary edema.

For developing measure of thermal bypass, an accurate appearance time is determined for the volume dilution value of thermal and conductivity signals. The difference in appearance time between the thermal and conductivity signals, or the area integral between their curves, provide a measure of thermal bypass.

BRIEF DESCRIPTION OF THE DRAWING

These and other features of the present invention are more fully setforth below in the solely exemplary detailed description and accompanying drawing of which.

DETAILED DESCRIPTION

In the present invention, in vivo detection of pulmonary edema is provided by detecting the response of the pulmonary vascular network to indicator dilution of thermal and conductivity modifiers as a function of not only detected thermal and conductivity values but additional body parameters including blood characteristics and a temperature modifier of conductivity. Values of mean transit time differences for the two indicators are developed to isolate the measurement system from recirculation effects and other noise errors. A value for extra vascular heat capacity is determined from which a quantified lung water measurement is obtained. A measure of indicator selective thermal bypass across the pulmonary thermal mass is developed.

Figure 1:
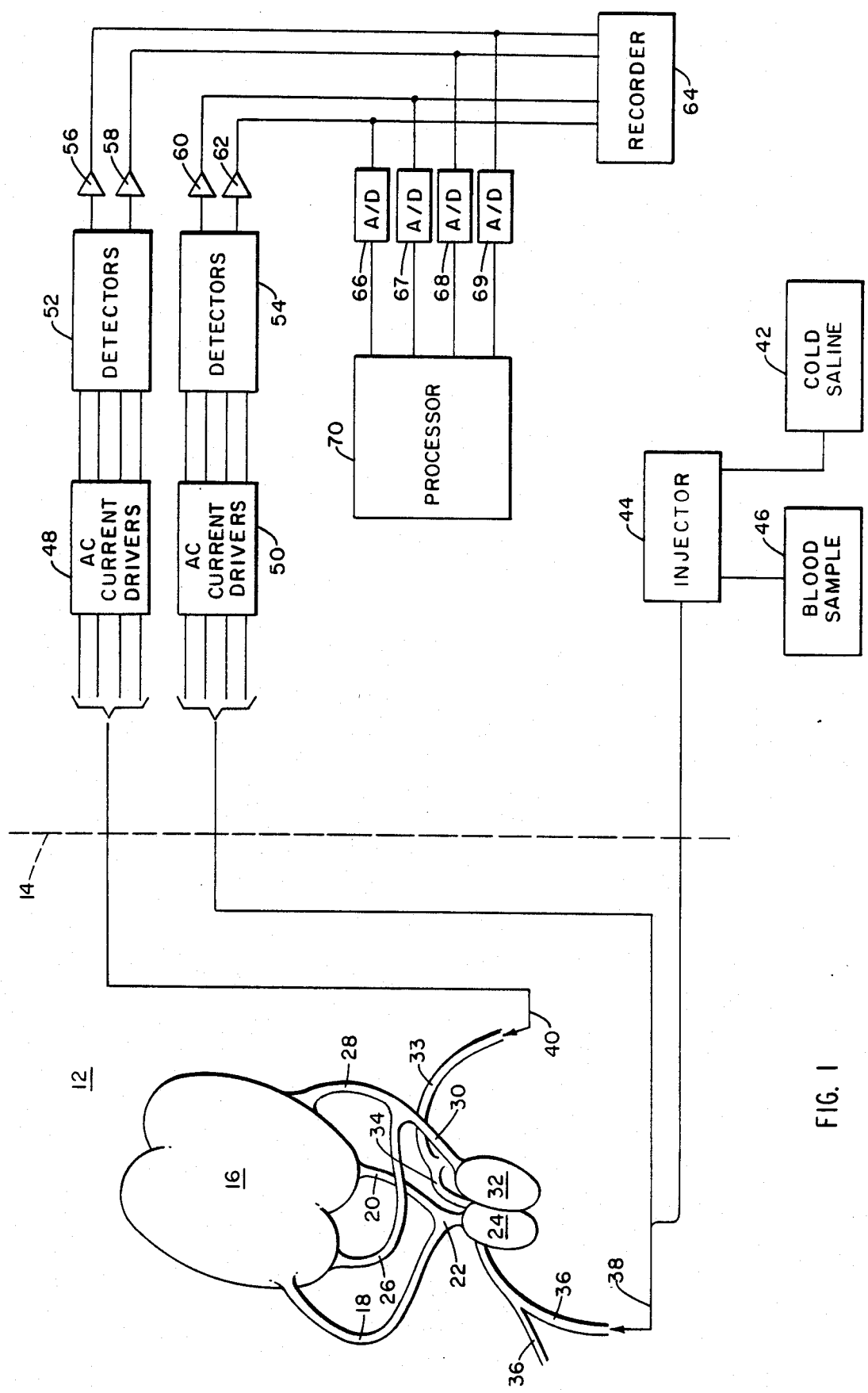
FIG. 1 is a diagram of apparatus for making double indicator, thermal and conductivity evaluations of pulmonary edema in accordance with the present invention.

A system for practicing the present invention is illustrated in FIG. 1 in which the in vivo region is generally represented as the region 12 to the left of a boundary 14 with the environment. In the body a set of lungs 16 receive a circulation of blood for oxygenation thereof through a pulmonary vascular system comprising a pair of pulmonary arteries 18 and 20 which branch from a unitary pulmonary arterial output 22 from the right ventricle of the right heart 24. Separate branches 26 and 28 of the pulmonary vein vessel 30 return oxygenated blood from the lungs 16 to the left auricle of the left heart 32 where it is pumped by cardiac contraction through the left ventricle to the aortic arch 34 from which it is distributed by the systemic arterial system 33 to other body regions, ultimately returning through the two vena cavae 36. For the purposes of detecting pulmonary edema as the presence of extra vascular lung water within the lungs 16, in accordance with the present invention, an indicator is applied to the circulatory system through insertion of a catheter 38 into one vena cava 36. The indicator is typically applied to the circulation system at this location in a vena cava from which it proceeds into the right heart 24 and out through the pulmonary artery 22. The catheter 38 provides lumens for injecting an indicator providing a dual modification of the properties of the blood flowing into the heart system from vena cava 36. This modifier is typically a cold saline solution providing both a modification in temperature and conductivity of the blood. The catheter 38 also includes a set of sensors, both a conductivity and a temperature sensor, located at a point downstream of the point of injection of the double indicator modifier. The sensors are typically located in the pulmonary artery. A catheter with a conductivity and thermal sensor system of this type is illustrated in commonly assigned co-pending U.S. patent application Ser. No. 099,710, filed Dec. 3, 1979.

A second catheter 40 is inserted into a large artery (e.g. femoral artery) of the systemic arterial system 33 and extended to a location which may be as far upstream as the aortic arch 34. The tip of catheter 40 includes both thermal and conductivity sensors similar to those of the catheter 38.

The injection of the cold saline into the vena cava 36 is provided from a reservoir 42 manually, or by a power injection and withdrawal unit 44. This provides injection of a known amount of heat, H, and of conductivity modifier, as a predetermined quantity of saline at a controlled temperature through the catheter 38. Directly subsequent to the injection, the unit 44 may withdraw a small amount of fluid through the same lumen of the catheter 38 to terminate the thermal injection more sharply. A separate sample of blood 46 is typically withdrawn before or after injection to permit conventional analyses of the blood values utilized below.

Figure 3A:
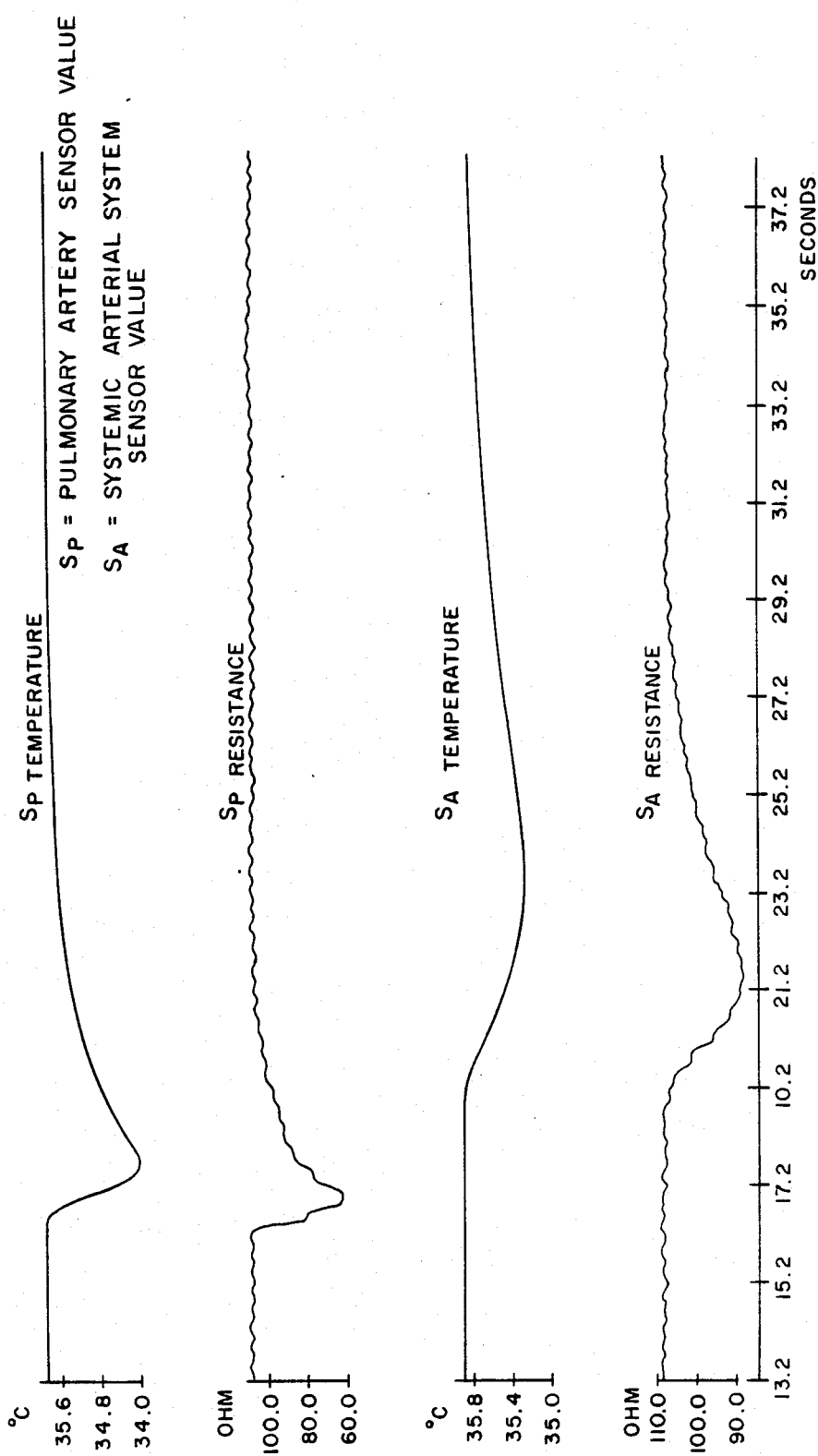
FIGS. 3A and 3B are sensor output and corresponding volume dilution curves obtained in practicing the present invention and useful in explaining it.

The conductivity and temperature sensors are typically conductivity cells and thermistors located on the catheters 38 and 40 within the respective pulmonary artery and arterial system. These sensors are driven by respective A.C. current drivers 48 and 50 which apply a predetermined current to the sensor resistances which in turn vary with the temperature or the conductivity of the surrounding blood. Signals representing the response of the applied current to the variable resistance, reflecting the temperature or conductivity being sought, are applied from the current drivers 48 and 50 to respective detectors 52 and 54 which detect their A.C. amplitude to provide a corresponding D.C. output. The detected amplitudes are in turn amplified by a set of amplifiers 56, 58, 60 and 62, one for each of the two conductivity and two temperature signals. A chart recorder 64 is provided to respond to the outputs of the amplifiers 56 through 62 to provide a continuous strip chart record of the magnitude of sensed temperature and conductivity in appropriate scale values as desired. FIG. 3A represents a typical recording of this nature.

The outputs of the amplifiers 56–62 are also applied through analog-to-digital conversion systems 66, 67, 68 and 69 for the catheters 38 and 40 respectively where the quantities are digitized and applied to a processor 70 wherein the ultimately desired extravascular lung water figures are determined from the inputs of sensed temperature and resistivity (conductivity) and the inputs of blood characteristics.

Figure 2:
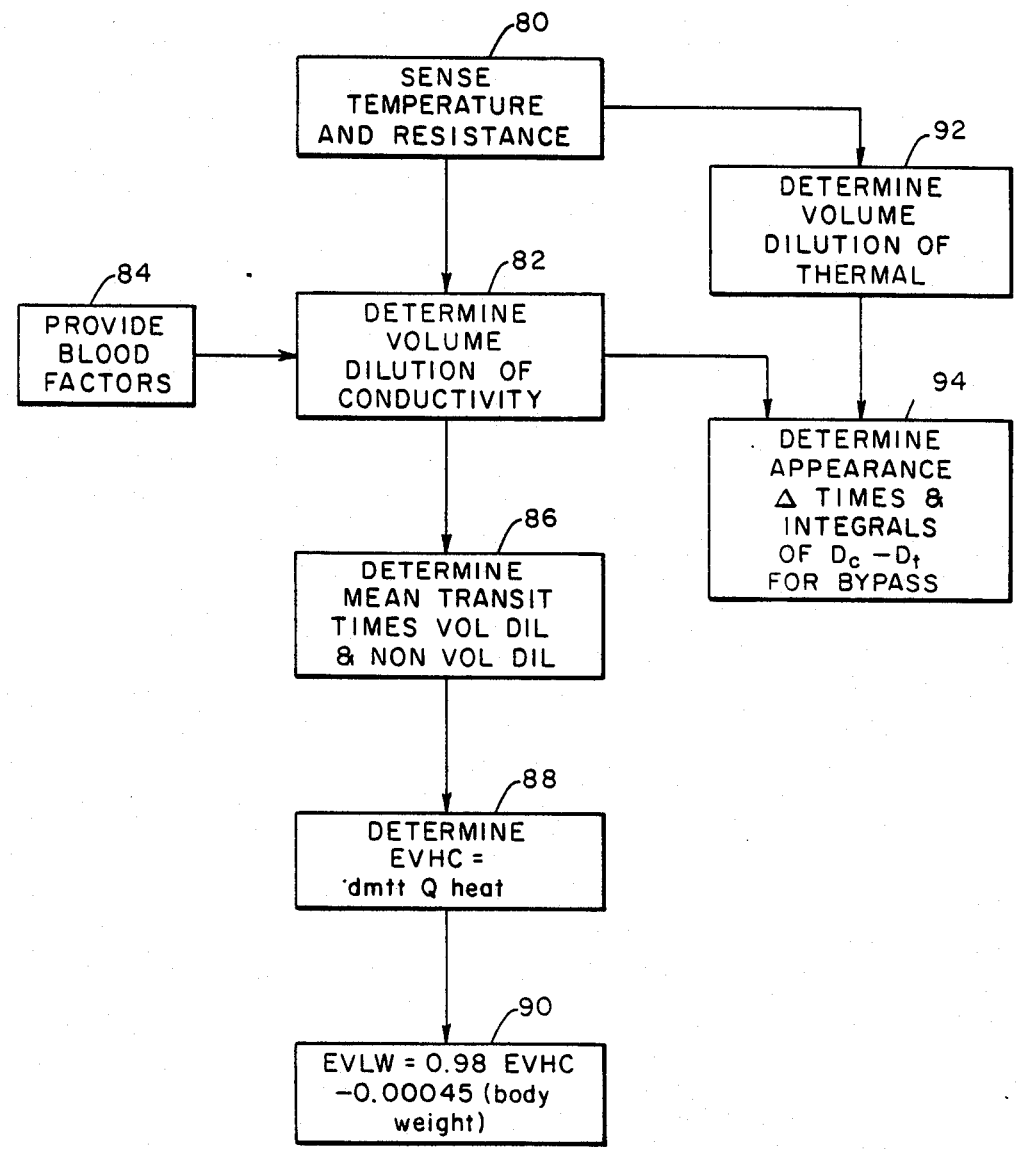
FIG. 2 illustrates the method of pulmonary edema and thermal bypass monitoring in accordance with the present invention.
Figure 3B:
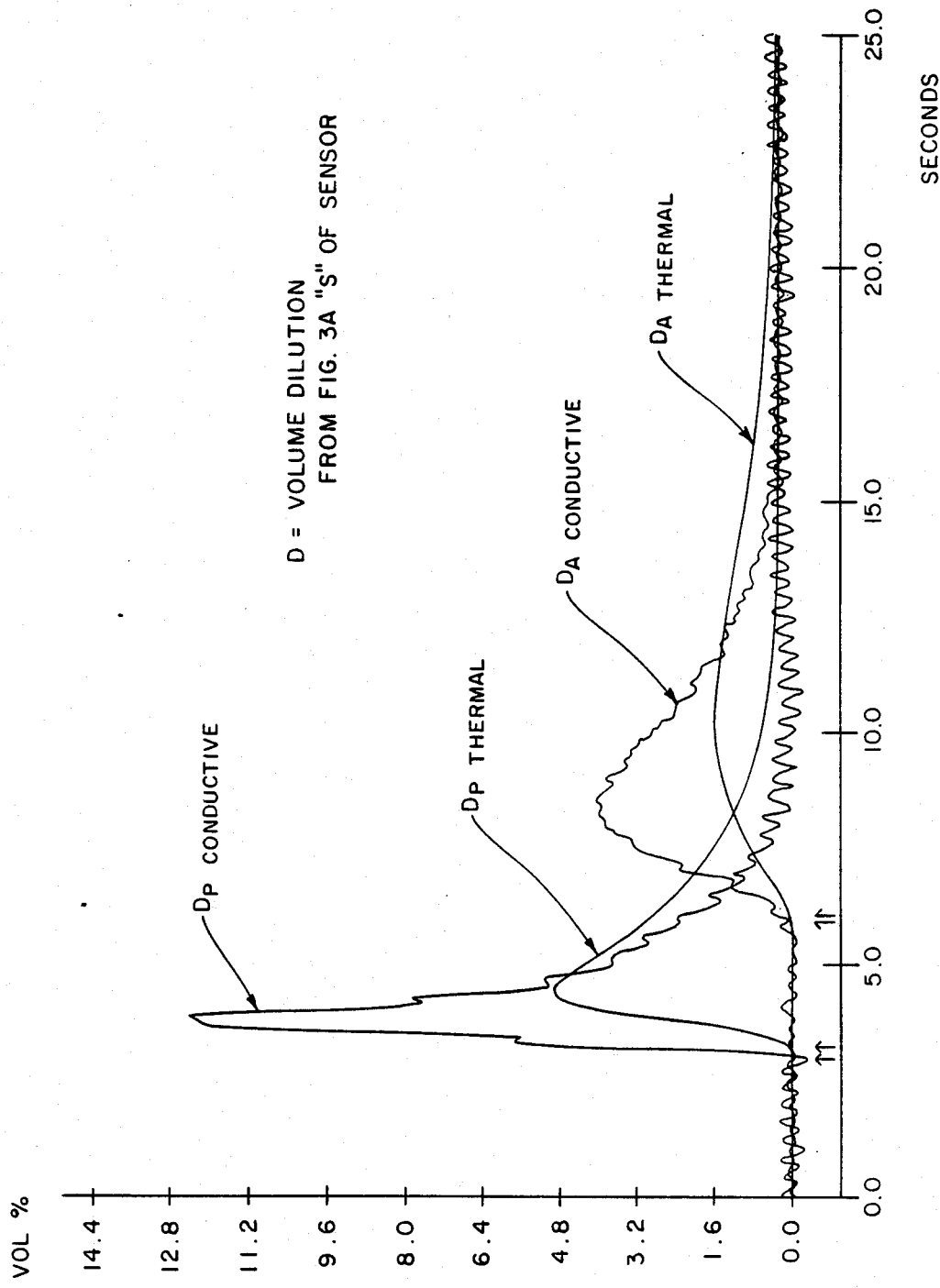

The method of determining pulmonary edema as an extra vascular lung water figure is illustrated with respect to FIG. 2 in conjunction with the waveform diagrams of FIG. 3A and FIG. 3B.

With respect now to FIG. 2, in a step 80, which typically, as with the other steps of FIG. 2, is under the control of processor 70, the output of the two temperature and two conductivity sensors as applied through the A-to-D converter 66–69 are recorded in a form of memory where they are available for further processing in accordance with FIG. 2. FIG. 3A shows a representation of such curves. A subsequent step 82 converts the conductivity curve values, on a point-by-point basis, to a volume dilution value in accordance with the FORTRAN processing steps of Tables IA and IB. TAble IA provides a definition for the variables used within the processing of Table IB. It is to be noted that this conversion of the conductivity output to a volume dilution curve proceeds as a function of not only resistivity, as sensed, but of temperature, as well as a series of blood and indicator factors including ion dissociation constant, blood and indicator osmolality, red cell form factor, hematocrit, fraction of immobilized charges, and water constants as defined there. These factors may be determined using conventional blood and fluid analysis in step 84, although in many cases these factors are significantly invariant from patient to patient and need not be redetermined from each blood sample 46 as is known in the art.

The volume dilution determination of Table IB is by the well known Newton method of successive approximations in which the volume dilution value, D, is successively approximated from a set of equations which define blood conductivity as a function of blood properties, temperature, injectate concentration and volume dilution itself. The successive approximation technique is utilized because these equations are not readily solvable for the volume dilution value alone as a function of the other variables. An alternative processing algorithm is illustrated in Table II which is useful only in the case of an isotonic saline indicator. In this situation the processing is more rapid and simple. The FORTRAN algorithm uses the same variables illustrated in Table IA.

With the volume dilution curves, D, determined in step 82, a subsequent step 86 determines the mean transit time from the volume dilution curves, D, for the two conductivity sensor outputs as provided in step 82 and also determines mean transit time from the sensed temperature curves directly. Table III represents the factors utilized in determining the mean transit times for the temperature and conductivity curves from both pulmonary artery locations and the systemic arterial system locations for the sensors. The conversions are essentially the ratios of a time to area integral of the temperature curve or the volume dilution curve in the case of conductivity. The integral is taken from zero to infinity but in practice proceeds between an appearance time defined as the point where the curve deviates from the baseline background value to a predetermined percentage of fall from peak of the real curve and is then corrected by an exponential best fit to the down slope. The integrations typically proceed by digital integration techniques as known in the art.

With the four mean transit times determined, a step 88 provides a determination of the extravascular heat capacity as a number which is equal to the mean transit time differences multiplied by the flow of heat capacity as presented in Table IV. The flow of heat capacity is determined as the ratio of the predetermined injected heat quantity, H, noted above, to the integral of, for example, one temperature sensor output, over the limits zero to infinity. The flow of heat capacity could be determined from any of the temperature or conductivity curves, while for practical purposes, it is typical to select one of the temperature curves, typically from the sensor at the pulmonary artery.

The detection system can be simplified by deleting the upstream sensors associated with catheter 38 (FIG. 1) and the electronics used with them. In this case, the results of Table IV are approximated by use of the same formula with the pulmonary, or upstream, transit times deleted, or assumed to be identical. While this approach is not preferred, it is likely to be adequate in many clinical applications. The corrections to conductivity for blood properties, including temperature, hematocrit, and plasma factors still are utilized and provide for enhanced accuracy in lung water detection.

With the extravascular heat capacity determined, a final step 90 provides a value for the actual extravascular lung water as 98% of the extravascular heat capacity reduced by a small fraction of body weight which number approximates the residual lung dry weight. This cannot be determined precisely without sacrificing the patient which is, of course, not desired.

In order to provide a measure of the thermal bypass, which reflects a transport of heat between its injection site and the systemic arterial system where temperature and conductivity are sensed, other than through the thermal mass of the lungs directly adjacent to blood vessels, additional processing of FIG. 2 is utilized. The thermal bypass reflects a component of sensed temperature which does not appear in sensed conductivity, and is, therefore, among other things, a measure of the thermal mass of the pulmonary system or other volume bypassed. The processing includes a step 92 in which volume dilution curves for sensed temperature are also determined using the relationship of Table V. Again, a determination is made for each of the thermal signals from the pulmonary arterial sensor location as well as the sensor placed in the systemic arterial system. Finally, a step 94 determines the difference in appearance times between the temperature and the conductivity volume dilution curves. While the appearance time may be estimated by comparison of the volume dilution curves as illustrated in FIG. 3B, it is preferable to determine an exact appearance time for each of the four curves using a correlation technique represented by Table VI. The correlation is with template which determines the optimal fit between that template and the volume dilution curve being considered. With these appearance times, the difference between the appearance times for the two temperature sensors in the volume dilution curves will differ from the difference between the appearance times for the two conductivity sensors as represented in their volume dilution curves. That overall difference is a measure of the degree of a thermal bypass. A more specific volume related measure of the thermal bypass is provided in step 94 as the integral of the difference between the volume dilution curves for conductivity and temperature from the sensors in the systemic arterial system with the appearance times for the pulmonary artery located sensors adjusted into coincidence.

The above described invention provides a method and apparatus for the determination of an accurate absolute extravascular lung water value as well as a quantitative and qualitative indicator external bypass. It is to be noted that modifications and improvements to the specific system may be made to the invention as defined solely in the following claims.

TABLE IA

VARIABLE IDENTIFICATION

| Name in calling sequence: | Description | Normal Value |
|---|---|---|
| D | present estimate of dilution | 0–0.99 |
| RES | resistivity in ohm-cm from sensor | 150. |
| TEMP | temperature in °C. from sensor | 37. |
| in COMMON: | (from Blood analysis) | |
| INIT | set to 0 when H changes | 99 |
| ALPHA | ion dissociation constant | 1.85 |
| BBL | OSMBL-ALPHA* (blood ion concentration) | 10. |
| OSMBL | osmolality of blood | 300. |
| FF | form factor | 1.05 |
| H | hematocrit | 0.40 |
| WBL | w (fraction of immobilized charges) of blood | 0.20 |
| BIN | OSMIN-ALPHA* (indicator ion concentration) | 0. |
| OSMIN | osmolality of indicator | 300 |
| WIN | w (fraction of mobilized charges) of indicator | 0. |
| XIW | indicator water content | 1.0 |
| CW | cell water content | 0.57 |
| PW | plasma water content | 0.94 |

A1, A2, B1, B2 equivalent conductivity constants (These constants are valid for sensed diluted concentrations of 100–200 milli equivalents per liter - for values outside this range modified constants can be obtained from the International Critical Tables.)

TABLE IB

Point by Point Calculation of Dilution for a General Indicator

```
    FUNCTION DINCR (D, RES, TEMP)
C   THIS FUNCTION RETURNS THE INCREMENT IN
    DILUTION OF A
C   GENERAL INDICATOR FOR
C   THE GIVEN RESISTIVITY AND TEMPERATURE
C   NECESSARY TO IMPLEMENT NEWTON'S METHOD
```

TABLE IB-continued
Point by Point Calculation of Dilution for a General Indicator

```
         OF APPROXIMATION
         COMMON /DDAT/ INIT, ALPHA, BBL, OSMBL,
         FF, H, WBL
         COMMON /CONST/ A1, A2, B1, B2
         COMMON /D DAT2/ BIN, OSMIN, WIN, XIW, CW, PW
         COMMON /DIEX/ OMH, BW
C        CONSTANTS COME FROM ANOTHER PROGRAM
         WHICH DETERMINE THE RANGE
C        DATA INIT/0/
C        DATA A1, A2, B1, B2, /-6. 19908E-3,3. 113E-7,-
         1. 40206E-3,6.2E-9/
C        SEE IF FIRST TIME --- SAVE COMPUTING TIME
         IF (INIT.NE.0) GOTO 100
         INIT=99
         OMH=1.-H
         BW=OMH*PW+H*CW
100      OMD=1.-D
         A1X=A1+1/(TEMP+273.15)
C        CALCULATE THE NEW CONCENTRATIONS
         OSMX=(OMD*OSMBL*BW+
         D*XIW*OSMIN)/(OMD*BW+D*XIW)
         SE1=H* (1.-CW*(1.-OSMBL/OSMX))
         XNH=OMD*SE1
         OMXNH=1.-XNH
         XNW=(WBL*OMH*OMD+WIN*D)/OMXNH
         XNB=(BBL*OMH*OMD+BIN*D)/OMXNH
         XI=(OSMX-XNB)* (OMD*PW+D*XIW)/ALPHA
         DXI=XI-100.
         XLAMD=10**((A1X+A2*DXI)/(B1+B2*DXI))
C        CALCULATE THE NEW DERIVATIVES
         DOSDD=(OSMIN-OSMBL)*XIW*BW/(BW*OMD+
         XIW*D)**2
         DNHDD=-CW*OMD*H*OSMBL*DOSDD/OSMX**2 -
         SE1
         DNWDD=((OMD*OMH*WBL+
         D*WIN)*DNHDD)/OMXNH**2 +
         (WIN-OMH*WBL)/OMXNH
         DNBDD=((OMD*OMH*BBL+
         D*BIN)*DNHDD)/OMXNH**2 +
         (BIN-OMH*BBL)/OMXNH
         DIDD=((DOSDD-DNBDD)*(OMD*PW+D*XIW)+
         (XIW-PW)*(OSMX-XNB))/ALPHA
C        CALCULATE THE "GRADS": F'/F
         GLAMD=2.302585*(A2*B1-A1X*B2)/(B1+B2*DXI)**2
         GDFH=DNHDD*(1.+.FF)/(OMXNH*(XNH+FF))
         GDFW=DNWDD/1.-XNW)
         GDFI=-DIDD*(GLAMD+1./XI)
C        CALCULATE THE FUNCTIONS
         FH=(1.+XNH/FF)/OMXNH
         FW=1/(1.-XNW)
         FI=1.0E6/(XLAMD * XI)
C        CALCULATE THE INCREMENT TO D
         DINCR=-(1.-RES/(FH*FW*FI)) / (GDFH+
         GDFW+GDFI)
         RETURN
         END
C        FINAL D USED FOR VOLUME DILUTION VALUE
```

TABLE II
Point By Point Calculation of Dilution for an Isotonic Indicator

```
         FUNCTION XSODIL(RES,TEMP)
C        THIS FUNCTION RETURNS THE DILUTION OF
         AN ISOTONIC INDICATOR FOR
C        THE GIVEN RESISTIVITY AND TEMPERATURE
         COMMON /DDAT/ INIT, ALPHA, BBL, OSMBL,
         FF, H, W
         COMMON /CONST/ A1, A2, B1, B2
         COMMON EXPR/ A,B,C,D,E,F,G,B3,XLAM2,XIONS
         DATA INIT/0/
         DATA A1,A2,B1,B2/-6. 19908E-3,3. 113E-7,-
         1. 40206E-3, 6.2E-9/
C        IF (INIT.NE.0)GOTO 100
         INIT=99
         OMH=1.-H
         A=(FF*OMH*(OSMBL*W-BBL))**2
         B=2.*ALPHA/PW*FF*OMH*((FF+1)*(W*OSMBL+
         BBL*(1-2.*W))*H
         1 +2. *BBL*W*(H+FF))
         C=(ALPHA/PW*(FF+1)*H)**2
         D=FF*OMH*(2.*H*(OSMBL-BBL)*(W-1)+
         W*(BBL-OSMBL)+BBL*(W-1)).
         E=ALPHA/PW*H*(H+FF-OMH)
         F=2*FF*(OSMBL*H+BBL*OMH)*H+OMH*W)
         G=2*ALPHA/PW*H**2
C        CORRECTIONS TO WATER CONTENT WOULD
         IMPROVE THIS
         XIONS=(OSMBL-BBL)/ALPHA*PW
         DELI=XIONS-100.
         B3=B1+B2*DELI
         XLAM2=10.**((A1+A2*DELI)/B3)*1.0E-6
C        ITERATIONS ON XIONS ARE POSSIBLE TO
         IMPROVE XLAM1
100      XLAM1=10.**(1./((TEMP+273.15)*B3))
         Z=RES*XLAM1*XLAM2
         XSODIL=(SQRT(A*Z**2+B*Z+C)+D*Z+E)/(F*Z+G)
         RETURN
         END
```

TABLE III $$\bar{t}_{A\ thermal} = \frac{\int_a^b t\, T_A(t)dt + C}{\int_a^b T_A(t)dt + K}$$

a = appearance time of the first curve to appear
b = 30% peak
$T_A$ = Sensor Temperature (minus baseline), Systemic Arterial System $$\bar{t}_{P\ thermal} = \frac{\int_a^b t\, T_P(t)dt + C}{\int_a^b T_P(t)dt + K}$$

a = appearance time of the first curve to appear
b = 30% peak
$t_P$ = Sensor Temperature (minus baseline), Pulmonary artery $$\bar{t}_{A\ cond} = \frac{\int_a^b t\, D_A(t)dt + C}{\int_a^b D_A(t)dt + K}$$

a = appearance time of the first curve to appear
b = 30% peak
$D_A$ = Volume Dilution Curve Systemic Arterial System Sensor $$\bar{t}_{P\ cond} = \frac{\int_a^b t\, D_P(t)dt + C}{\int_a^b D_P(t)dt + K}$$

a = appearance time of the first curve to appear
b = 15% peak
$D_P$ = Volume Dilution Curve Pulmonary Artery Sensor $C = -(e^{Tx+B})/x$; $K = (T - 1/x)C$ with $T = t$ at b and $e^{Tx+B}$ = fitted exponential function for respective curve

TABLE IV

EVHC = dmtt Qheat
dmtt = $(\bar{t}_{A\ thermal} - \bar{t}_{P\ thermal})$
     = $-(\bar{t}_{A\ cond} - \bar{t}_{P\ cond})$
Qheat = flow of heat capacity

TABLE IV-continued $$= \frac{H}{\int T(t)dt}$$

where any T (sensed temperature minus baseline) can be used, and H = injected heat quantity

TABLE V $$D_{thermal} = \frac{P_B CP_B(T - T_B)}{P_B CP_B(T - T_B) - P_I CP_I(T - T_I)}$$

Where PCP = density specific heat product of Blood (B) or indicator (I) from prior knowledge or laboratory analysis.
T = Temperature as sensed in Pulmonary artery or systemic arterial system.
$T_I$ = Indicator Temperature as injected
$T_B$ = Blood inflow temperature (preinjection T or upstream sensor)

TAVLE VI $$corr(n) = \sum_{i=-M}^{N} D(n + i) \text{Template}(i)$$

Template(n,a) = o, n ≤ 0

$$= \frac{n^2}{n + a}, n > o$$

M is number of prior samples in curve segment.
N is number of subsequent samples in curve segment.
choose "a" (o < a < 10) for which maximum correlation is obtained;
time at which maximum correlation for that a occurs defines appearance time in terms of n.

What is claimed is:

1. A method for measuring extra vascular lung water in vivo comprising the steps of:
   injecting a temperature and conductivity modifier into the blood circulatory system in a location whereby the modifier passes through the pulmonary vascular system;
   measuring temperature and conductivity in the circulatory system downstream of the point of modifier injection including respective locations upstream and downstream of the pulmonary vascular system to provide two temperature and two conductivity measurements;
   The injection of the thermal diluent causing a disturbance in the measured conductivity;
   adjusting the measured conductivity as a function of at least one property other than hematocrit of blood selected from the group consisting of temperature, osmolality, red cell form factor, water content and ion dissociation factor whereby the disturbance of the thermal diluent on measured conductivity is corrected; and
   determining the extra vascular lung water value from measured temperature and adjusted conductivity.

2. The method of claim 1 wherein said adjusting step includes providing a volume dilution value for each measured conductivity.

3. The method of claims 1 or 4 wherein said determining step includes determining the overall mean transit time differences for temperature and adjusted conductivity.

4. The method of claim 1 wherein:
   said injecting step includes injecting a temperature and conductivity modifier in a vena cava, ahead of the right heart;
   said measuring step includes measuring temperature and conductivity in the pulmonary artery and measuring temperature and conductivity in the systemic arterial system.

5. The method of claim 1 wherein said injecting step includes the step of injecting a cold saline solution.

6. The method of claim 1 wherein:
   said measuring step includes the step of determining from measured temperature the volume dilution of temperature separately for the pulmonary artery and systemic arterial system;
   a step is included for determining a measure of thermal bypass from the volume dilution of conductivity and temperature.

7. The method of claim 1 further including the step of adjusting conductivity for hematocrit.

8. A method for detecting thermal bypass in a circulatory system comprising the steps of:
   applying a modifier of temperature and conductivity to a circulatory system including a thermal mass;
   detecting volume dilution values as a function of time for temperature and conductivity, at at least two separate locations in said circulatory system, one upstream and one downstream of said thermal mass, in response to the applied modifier of temperature and conductivity;
   determining a measure of thermal bypass from said detected volume dilution values.

9. The method of claim 8 wherein said determining step includes determining the overall difference in temperature and conductive volume dilution appearance time between said separate locations.

10. The method of claim 8 wherein said determining step includes determining the area between the detected volume dilution values for the downstream location, with the upstream location volume dilution values adjusted into coincidence at their respective times of appearance.

11. Apparatus for measuring extra vascular lung water in vivo comprising:
    means for injecting a temperature and conductivity modifier into the blood circulatory system in a location whereby the modifier passes through the pulmonary vascular system;
    means for measuring temperature and conductivity in the circulatory system downstream of the point of modifier injection including respective locations upstream and downstream of the pulmonary vascular system to provide two temperature and two conductivity measurements;
    the injection of the thermal diluent causing a disturbance in the measured conductivity;
    means for adjusting the measured conductivity as a function of at least one property other than hematocrit of blood selected from the group consisting of temperature, osmolality, red cell form factor, water content and ion dissociation factor whereby the disturbance of the thermal diluent on measured conductivity is corrected; and
    means for determining the extra vascular lung water value from measured temperature and adjusted conductivity.

12. The apparatus of claim 11 wherein said adjusting means includes means for providing a volume dilution value for each measured conductivity.

13. The apparatus of claims 11 or 19 wherein said determining means includes means for determining the overall mean transit time differences for temperature and adjusted conductivity.

14. The apparatus of claim 11 wherein:
said injecting means includes means for injecting a temperature and conductivity modifier in a vena cava, ahead of the right heart;
said measuring means includes means for measuring temperature and conductivity in the pulmonary artery and measuring temperature and conductivity in the systemic arterial system.

15. The apparatus of claim 11 wherein said injecting step includes the step of injecting a cold saline solution.

16. The apparatus of claim 11 wherein:
said measuring means includes means for determining from measured temperature the volume dilution of temperature separately for the pulmonary artery and systemic arterial system;
means are included for determining a measure of thermal bypass from the volume dilution of conductivity and temperature.

17. The apparatus of claim 11 wherein said adjusting means is further adapted to adjust measured conductivity as a function of hematocrit in addition to said at least one other blood property.

18. Apparatus for detecting thermal bypass in a circulatory system having a thermal mass comprising:
means for applying a modifier of temperature and conductivity to said circulatory system;
means for detecting volume dilution values as a function of time for temperature and conductivity, at at least two separate locations in said circulatory system, one upstream and one downstream of said thermal mass, in response to the applied modifier of temperature and conductivity;
means for determining a measure of thermal bypass from said detected volume dilution values.

19. The apparatus of claim 18 wherein said determining means includes means for determining the overall difference in temperature and conductivity volume dilution appearance time between said separate locations.

20. The apparatus of claim 18 wherein said determining step includes determining the area between the detected volume dilution values for the downstream location, with the upstream location volume dilution values adjusted into coincidence at their respective times of appearance.

* * * * *